(12) United States Patent
Khanuja et al.

(10) Patent No.: US 7,262,004 B1
(45) Date of Patent: Aug. 28, 2007

(54) SCREENING METHOD FOR SELECTION OF INSECT TOLERANT PLANTS

(75) Inventors: Suman Preet Singh Khanuja, Lucknow (IN); Ajit Kumar Shasany, Lucknow (IN); Sunita Dhawan, Lucknow (IN); Mahendra Pandurang Darokar, Lucknow (IN); Sarita Satapathy, Lucknow (IN); Tiruppadiripuliyur Ranganathan Santha Kumar, Lucknow (IN); Dharmendra Saikia, Lucknow (IN); Nirmal Kumar Patra, Lucknow (IN); Janak Raj Bahl, Lucknow (IN); Arun Kumar Tripathy, Lucknow (IN); Sushil Kumar, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/487,405

(22) Filed: Jan. 18, 2000

(51) Int. Cl.
*C12Q 1/68* (2006.01)

(52) U.S. Cl. .................... 435/6; 435/91.2; 435/91.1; 800/302

(58) Field of Classification Search .............. 800/100, 800/205, 200, 230, 320.1, 302; 435/240.4, 435/45.49, 412, 429, 430, 430.1, 6, 91.1, 435/91.2; 536/24.3; 935/6; 436/518
See application file for complete search history.

(56) References Cited

U.S. PATENT DOCUMENTS

PP8,645 P * 3/1994 Sturtz ...................... Plt./100
5,436,395 A * 7/1995 Sondahl et al. ............. 800/230
5,898,001 A * 4/1999 Kumar et al. ............... 435/430
6,187,999 B1 * 2/2001 Gilbert .................... 800/320.1

OTHER PUBLICATIONS

Jones et al., "Soybean resistance to the Southern Green Stink Bug, *Nesara viridula*", *Journal of Economic entomology*, (1979), vol. 72, pp. 628-632.*

Prajapati et al., "Sensitivity of Spilarctica obliqua to root extracts of *Catharanthus roseues*", *Phytotherapy research*, vol. 12, pp. 270-274, 1998.*

Brigden (Hortscience (1996), vol. 31, No. 4, p. 695, abstract # 764).*

Khanuja et al. (Journal of Medicinal and Aromatic Plant Sciences, 1998, vol. 20, p. 359-361).*

* cited by examiner

*Primary Examiner*—Juliet Switzer
(74) *Attorney, Agent, or Firm*—Ladas & Parry LLP (57) ABSTRACT

An in vitro screening method for identifying insect tolerant genotypes or clones is described. The method comprises growing plantlets in an in vitro system, screening the plantlets for molecular variation of somaclones using RAPD analysis in vitro, selecting the somaclones having molecular variation, exposing the somaclones to insect larvae or nymphs and identifying the surviving somaclones.

8 Claims, 4 Drawing Sheets
(3 of 4 Drawing Sheet(s) Filed in Color)

```
                        SEQUENCE LISTING

<160> NUMBER OF SEQ ID NOS: 20

<210> SEQ ID NO 1
<211> LENGTH: 10
<212> TYPE: DNA
<213> ORGANISM: Artificial Sequence
<220> FEATURE:
<223> OTHER INFORMATION: MAP Primer

<400> SEQUENCE: 1
aaatcggagc                                                          10

<210> SEQ ID NO 2
<211> LENGTH: 10
<212> TYPE: DNA
<213> ORGANISM: Artificial Sequence
<220> FEATURE:
<223> OTHER INFORMATION: MAP Primer

<400> SEQUENCE: 2
gtcctactcg                                                          10

<210> SEQ ID NO 3
<211> LENGTH: 10
<212> TYPE: DNA
<213> ORGANISM: Artificial Sequence
<220> FEATURE:
<223> OTHER INFORMATION: MAP Primer

<400> SEQUENCE: 3
```

-continued gtccttagcg    10

<210> SEQ ID NO 4
<211> LENGTH: 10
<212> TYPE: DNA
<213> ORGANISM: Artificial Sequence
<220> FEATURE:
<223> OTHER INFORMATION: MAP Primer

<400> SEQUENCE: 4
tgcgcgatcg    10

<210> SEQ ID NO 5
<211> LENGTH: 10
<212> TYPE: DNA
<213> ORGANISM: Artificial Sequence
<220> FEATURE:
<223> OTHER INFORMATION: MAP Primer

<400> SEQUENCE: 5
aacgtacgcg    10

<210> SEQ ID NO 6
<211> LENGTH: 10
<212> TYPE: DNA
<213> ORGANISM: Artificial Sequence
<220> FEATURE:
<223> OTHER INFORMATION: MAP Primer

<400> SEQUENCE: 6
gcacgccgga    10

<210> SEQ ID NO 7
<211> LENGTH: 10
<212> TYPE: DNA
<213> ORGANISM: Artificial Sequence
<220> FEATURE:
<223> OTHER INFORMATION: MAP Primer

<400> SEQUENCE: 7
caccctgcgc    10

<210> SEQ ID NO 8
<211> LENGTH: 10
<212> TYPE: DNA
<213> ORGANISM: Artificial Sequence
<220> FEATURE:
<223> OTHER INFORMATION: MAP Primer

<400> SEQUENCE: 8
ctatcgccgc    10

<210> SEQ ID NO 9
<211> LENGTH: 10
<212> TYPE: DNA
<213> ORGANISM: Artificial Sequence
<220> FEATURE:
<223> OTHER INFORMATION: MAP Primer

<400> SEQUENCE: 9
cgggatccgc    10

<210> SEQ ID NO 10
<211> LENGTH: 10
<212> TYPE: DNA

-continued

```
<213> ORGANISM: Artificial Sequence
<220> FEATURE:
<223> OTHER INFORMATION: MAP Primer

<400> SEQUENCE: 10
gcgaattccg                                                              10

<210> SEQ ID NO 11
<211> LENGTH: 10
<212> TYPE: DNA
<213> ORGANISM: Artificial Sequence
<220> FEATURE:
<223> OTHER INFORMATION: MAP Primer

<400> SEQUENCE: 11
ccctgcaggc                                                              10

<210> SEQ ID NO 12
<211> LENGTH: 10
<212> TYPE: DNA
<213> ORGANISM: Artificial Sequence
<220> FEATURE:
<223> OTHER INFORMATION: MAP Primer

<400> SEQUENCE: 12
ccaagcttgc                                                              10

<210> SEQ ID NO 13
<211> LENGTH: 10
<212> TYPE: DNA
<213> ORGANISM: Artificial Sequence
<220> FEATURE:
<223> OTHER INFORMATION: MAP Primer

<400> SEQUENCE: 13
gtgcaatgag                                                              10

<210> SEQ ID NO 14
<211> LENGTH: 10
<212> TYPE: DNA
<213> ORGANISM: Artificial Sequence
<220> FEATURE:
<223> OTHER INFORMATION: MAP Primer

<400> SEQUENCE: 14
aggatacgtg                                                              10

<210> SEQ ID NO 15
<211> LENGTH: 10
<212> TYPE: DNA
<213> ORGANISM: Artificial Sequence
<220> FEATURE:
<223> OTHER INFORMATION: MAP Primer

<400> SEQUENCE: 15
aagatagcgg                                                              10

<210> SEQ ID NO 16
<211> LENGTH: 10
<212> TYPE: DNA
<213> ORGANISM: Artificial Sequence
<220> FEATURE:
<223> OTHER INFORMATION: MAP Primer

<400> SEQUENCE: 16
ggatctgaac                                                              10
```

```
<210> SEQ ID NO 17
<211> LENGTH: 10
<212> TYPE: DNA
<213> ORGANISM: Artificial Sequence
<220> FEATURE:
<223> OTHER INFORMATION: MAP Primer

<400> SEQUENCE: 17
ttgtctcagg                                                           10

<210> SEQ ID NO 18
<211> LENGTH: 10
<212> TYPE: DNA
<213> ORGANISM: Artificial Sequence
<220> FEATURE:
<223> OTHER INFORMATION: MAP Primer

<400> SEQUENCE: 18
catcccgaac                                                           10

<210> SEQ ID NO 19
<211> LENGTH: 10
<212> TYPE: DNA
<213> ORGANISM: Artificial Sequence
<220> FEATURE:
<223> OTHER INFORMATION: MAP Primer

<400> SEQUENCE: 19
ggactccacg                                                           10

<210> SEQ ID NO 20
<211> LENGTH: 10
<212> TYPE: DNA
<213> ORGANISM: Artificial Sequence
<220> FEATURE:
<223> OTHER INFORMATION: MAP Primer

<400> SEQUENCE: 20
agcctgacgc                                                           10
```

SCREENING METHOD FOR SELECTION OF INSECT TOLERANT PLANTS

FIELD OF INVENTION

The present invention relates to a novel method for screening, identifying and developing insect tolerant plant, genotypes or clones. The invention is the result of development of a novel devised procedure for early selection of somaclonal variants among the in vitro raised large population of a menthol rich superior variety of Mentha arvensis leading to generation of an insect tolerant mint plant with high oil and menthol yield. The plant can be propagated vegetatively by suckers and is genetically stable for commercial cultivation. The plant type is unique with the extra wide canopy and height surpassing all existing varieties permitting better sunlight capture and vigorous foliage production ultimately giving high oil and menthol yield. The procedure although applied to Mentha against lepidopteran insect pests can be employed for any plant of choice against all damaging insect pests.

BACKGROUND OF THE INVENTION

Mentha arvensis Linn. var piperescens. Holmes (menthol or Japanese mint) is an industrial crop that is widely cultivated for its essential oil from which menthol is purified by crystallization through freezing. Menthol and other terpenoids present in the dementholated oil of Mentha arvensis are variously used in the food, perfumery and pharmaceutical industries. In the varietal improvement programme the genetic alternations leading to enhancement in the tolerance against pest and disease and improving other adaptive characters determining the yield and quality of essential oil is most desirable. Insect tolerance is desired particularly against Spilarctia obliqua in mentha, which is the most damaging pest of mints in India. Since the mints are of considerable interest to the industrial world, selection programs for the isolation of desirable clones with improved terpene accumulation and suitable agronomic traits are being pursued in several laboratories. However, due to the inherent problem of seed setting in mints, conventional breeding programmes are severely hampered. In vitro high efficiency procedures for cell and callus cultures and shoot regeneration from axillary buds and leaf explants have been reported in some species of the genus Mentha, especially the commercially important species M. piperata and M. spicata.

However, in M. arvensis mostly the media used have permitted shoot proliferation from limited explants such as nodes, terminal and axillary buds and distal segments of leaf petiole at relatively low levels of efficiency. Attempts to develop new varieties or genotypes by alternative methods like clonal selection, mutation breeding and somaclonal variation have been followed in mints (S. P. S. Khanuja, A. K. Shasany, S. Dhawan, S. Kumar, Rapid procedure for isolating somaclones of altered genotypes in Mentha arvensis. J Med. Aroma. Plant Sci. 20 (1998) 359–361.). The applicants have reported high efficiency protocols for rapid detection and selection procedure for development of somaclonal variants through molecular approaches in Mentha arvensis (S. P. S. Khanuja, A. K. Shasany, S. Dhawan, S. Kumar, Rapid procedure for isolating somaclones of altered genotypes in Mentha arvensis. J Med. Aroma. Plant Sci. 20 (1998) 359–361). We have also successfully defined the conditions and media to restrict the emergence of somaclonal variation for stable micropropagation purposes (A. K. Shasany, S. P. S. Khanuja, S. Dhawan, U. Yadav, S. Sharma, S. Kumar, High regenerative nature of Mentha arvensis internodes. Journal of Biosciences 23 (1998) 641–646.).

In the present invention, the applicants have utilized the already reported protocol (S. P. S. Khanuja, A. K. Shasany, S. Dhawan, S. Kumar, Rapid procedure for isolating somaclones of altered genotypes in Mentha arvensis. J Med. Aroma. Plant Sci. 20 (1998) 359–361.) to generate and capture the somaclonal variations in larger frequencies. We, then screened the somaclones for their tolerance to Spilarctia obliqua by devising a novel method for rapid and dependable selection of tolerant clone(s) right at the tissue culture stage. Further the tolerant plants, which survived were tested for their stability, essential oil, menthol content and biomass yield. Consequently, the plant GRB2-18 was selected for unmatchable vigor of shoots, higher menthol production and increased insect tolerance through field evaluation.

BRIEF DESCRIPTION OF ACCOMPANYING DRAWINGS

The file of this patent contains at least one drawing or photograph executed in color. Copies of this patent with color drawing(s) or photograph(s) will be provided by the Patent and Trademark Office upon request and payment of necessary fee.

DETAILED DESCRIPTION

Breeding history:

Bihar hairy caterpillar (Spilarctia obliqua) is a major pest of polyphagus nature which infects heavily over a large area of mint crops frequently in Terai and north Indian plains. The infestation sometimes is so heavy and unmanageable that it may lead to more than 80% to complete loss of foliage and consequently the oil yield proportionately. Hence it is desirable to explore the possibility of developing insect tolerant high yielding clones in mints. The popular menthol mint variety "Himalaya" developed in 1996 by CIMAP (US Pat. No PP10935) was, therefore, used as the starting material for specific improvement towards insect tolerance through generation of somaclonal variation and simultaneously looking for improved plant type with higher essential oil and menthol yields.

Encouraged by the initial leads in the laboratory for rapid detection and isolation of somaclonal variants by using the protocol reported by us (S. P. S. Khanuja, A. K. Shasany, S. Dhawan, S. Kumar, Rapid procedure for isolating somaclones of altered genotypes in Mentha arvensis. J Med. Aroma. Plant Sci. 20 (1998) 359–361), we generated 3000 independent somaclones. These clones were subjected to detection of molecular variation at the tissue culture stage itself through RAPD profiling. DNA was isolated from 40 mg of leaf tissue and Polymerase chain reactions (PCRs) were carried out in 25 μl volume. A reaction tube contained 25 ng of DNA, 0.2 unit of Taq DNA polymerase, 100 μl each of dNTPs, 1.5 mM $MgCl_2$ and 5 p mol of decanucleotide primers. The amplifications were carried out using a thermal cycler (MJ Research, USA). The amplified products were loaded in 1.2% agarose gel containing 0.5 μg $ml^{-1}$ of ethidium bromide and photographed by Polaroid system. Twelve decamer primers having the sequences AAATCG-GAGC (SEQ ID NO: 1), GTCCTACTCG (SEQ ID NO: 2), GTCCTTAGCG (SEQ ID NO. 3), TGCGCGATCG (SEQ ID NO: 4), AACGTACGCG (SEQ ID NO. 5), GCACGC-CGGA (SEQ ID NO: 6), CACCCTGCGC (SEQ ID NO: 77), CTATCGCCGC (SEQ ID NO: 8), CGGGATCCGC (SEQ ID NO: 9), GCGAATTCCG (SEQ ID NO: 10), CCCTG-CAGGC (SEQ ID NO: 11), CCAAGCTTGC (SEQ ID NO: 12) were used to analyse all the in vitro regenerated clones. Out of 3000 regenerated clones 245 showed variation at DNA level in the RAPD profiles compared to the control plant "Himalaya".

The individual molecular variants selected through RAPD analysis of somaclones as above were then subjected to screening against the larvae of lepidopteran insect pest *Spilarctia obliqua*.

For this purpose, a new strategy was devised by subjecting the in vitro growing clones to attack by actively feeding $3^{rd}$ instar larvae by releasing them right in the culture tubes containing individual clones on the rooting medium (Sheet # 3, Photograph # 1).

Most of the shoots of the clones were eaten away by these larvae within 2-3 days.

However, three clones showed the least feeding by the larvae. In these tubes, only initial bites could be observed and nonfeeding was also conspicuous by typical symptoms of stalled growth in the starved larvae. These larvae were then transferred to other clone tubes, where they resumed feeding. This led to the applicants to believe that the three clones must have some characteristics not liked by the feeding larvae. So the applicants again confirmed this by releasing another set of actively feeding $4^{th}$ instar larvae into the tubes containing these three identified clones. This process was repeated three times and each time, the larvae showed non-preference and stopped feeding.

The applicants then hardened these three "insect-non-preferred" clones namely, CIMAP/GRB 1-06, 2-18 and 5-15 and transferred to the glasshouse in pots. Among these three clones, CIMAP/GRB 2-18 showed conspicuously vigorous growth characteristics attaining much higher height and shoot proliferation. This clone GRB 2-18 was multiplied in vitro from internodal explants through stable micropropagation protocol developed in the laboratory (A. K. Shasany, S. P. S. Khanuja, S. Dhawan, U. Yadav, S. Sharma, S. Kumar, High regenerative nature of *Mentha arvensis* internodes. Journal of Biosciences. 23 (1998) 641–646.) for genetic uniformity into about 1000 plantlets. Randomly 100 regenerated shoots from the clone were tested for variation in their profiles using the above described 12 random primers. Complete uniformity was observed among these clones without any variation from the control mother plant GRB 2-18 but the profiles were clearly distinct from other mint varieties including "Himalaya".

Figure 2:
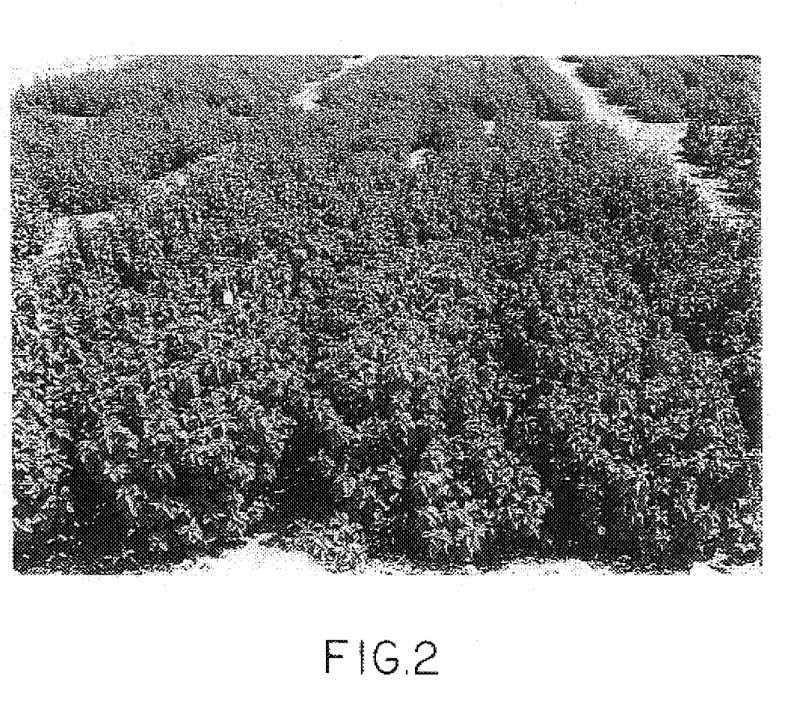
FIG. 2 shows field view of the morphological features of the 'Sambhav' plants at 100 days.

The overall objective of the invention was not only to develop insect tolerant genotypes but simultaneously also have better plant type with high menthol content and herbage yield for better productivity. So, the plant of invention was tested in field trial for oil yield, menthol content and herbage production against the checks (varieties developed by CIMAP). Replicated field trials were conducted following normal agronomic practices by planting multiplied suckers in the month of January, 1998 and 1999 for 2 consecutive years in RBD fashion and different growth and yield characteristics were recorded (Table 1). For field trials 10 m×10 m plots were prepared by adding only FYM 1.5 ton per ha. Astonishingly the plant CIMAP/GRB 2-18 was able to out-compete all existing varieties in its rate of growth. It was so rapidly growing that it could cover the inter-row spacing of 80 cm completely within a period of 90–100 days, which was not the case of other control varieties taken (FIG. 2). The plant canopy covered a space of 85 to 90 cm in 110 days in comparison to Himalaya(62–70 cm), Shivalik (50–56 cm), Gomti (70–75), Kosi (65–72), Kalka (40–60 cm) and MAS-1 (40–50 cm). This was the most desirable advantage to the plant as it produced highest amount of herbage and ultimately the oil and menthol.

Natural infestation of *Spilarctia obliqua* in field in absence of insecticidal spray was scored in both 1998 and 1999 crop stands. The clone GRB 2-18 had less than 10% leaf damage compared to 86% in case of Gomti, 58% in Himalaya, 50% in Kosi in the year 1998. Similar trend was also recorded in 1999 when leaf damage was 70%, 50% and 46% for Gomti, Himalaya and Kosi, respectively compared to 6% in case of GRB 2-18. This plant of invention also produced highest amount of essential oil per unit area in comparison to the other control plant in both the successive yield trials. The total menthol yield consequently, was the highest due to more oil and herbage yield (Table 1). The plant was hence named "Sambhav" (means "Possible") that's so because the expression of its genotype made this rare but most desirable combination of traits of high level insect tolerance and plant type with rapid growth possible in a single plant.

Thus the plant of invention "Sambhav" combines expression of the character of very high tolerance to *Spilarctia obliqua* attack, high growth rate and regenerability while producing highest total herbage, oil and menthol yield per unit area in comparison to the other control plants and thereby being unique, novel genotype which can be exploited commercial cultivar superior to other available mint varieties for menthol production.

Accordingly, the invention provides a novel procedure to screen, identify and develop insect tolerant plant genotypes or clones wherein, a. the clones are generated through tissue culture as somaclones and their molecular distinctiveness is established prior to screening through RAPD analysis at in vitro stage itself, b. the clones could be generated vegetatively in tissue culture, glasshouse or field by asexual reproduction methods, c. the identified molecular variants are micropropagated for multiplication and checked for the stability at molecular level through RAPD among clones of larger population, d. the identified stable variants after being multiplied are transferred to individual culture tubes for forced feeding of insects by releasing actively feeding larvae or nymphs into each culture tube, e. the surviving clones are in-vitro multiplied and rechecked for insect larval non-preference and then field evaluated under natural or artificial insect infestation conditions, f. the procedure can be followed for mints and all other plants where raising somaclones or rapid propagation is amenable, and g. the larvae are lepidopteran but scope of invention is not limited to larvae of lepidopteran and can be any actively feeding stage of pests.

In an embodiment, the plants are raised by raising somaclones or rapid propagation method.

In another embodiment, a novel screening method useful for the selection and development of an insect tolerant mint plant genotypes or clones, said method comprising the steps of:

a) generating the clones of an insect tolerant plant through tissue culture as somaclones and establishing their molecular distinctiveness prior to screening through RAPD analysis at in vitro stage itself;

b) micro-propagating the identified molecular variants for multiplication and checking for the stability at molecular level through RAPD among clones of larger population, c) transferring the identified stable variants after being multiplied to individual culture tubes for forced feeding of insects by releasing actively feeding larvae or nymphs into each culture tube, d) multiplying in-vitro the surviving clones and rechecking for insect larval non-preference and then field evaluating under natural or artificial insect infestation conditions.

In still another embodiment, the scope of invention is not limited to larvae of lepidopteran and used and can be any actively feeding stage of pests.

In a further embodiment, the clones could be generated vegetatively in tissue culture, glass house or field by asexual reproduction method.

Figure 7:
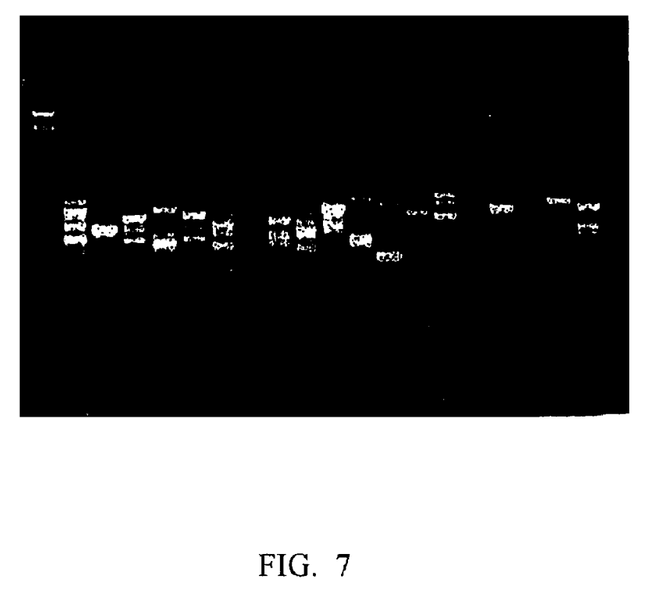
FIG. 7 shows RAPD profile of 'Sambhav'.

The invention in another embodiment provides a new and distinct mint plant.:

*Mentha arvensis* 'Sambhav' which is covered in a U.S. patent application Ser. No. 09/482,645 now U.S. Pat. No. PP 14,538 P2, developed through tissue culture, possessing the following combination of characters:

a. the plant is highly tolerant to the insect pest *Spilarctia obliqua,* b. the tolerance trait of the plant is not limited to *Spilarctia obliqua* which could be against other actively foliage feeding insect pests also, c. the plant possesses vigorous and rapid vegetative growth with high regenerability covering at least 85 cm canopy area and a height of at least 73.5 cm in a maximum of 100 days, d. the plant has distinct molecular profile by random amplified polymorphic DNA (RAPD) using 20 OPJ primers and 20 MAP primers distinguishing the plant from the other existing varieties (FIG. 7), e. the plant shows tolerance to leaf spot, rust and powdery mildew as in the parent variety 'Himalaya', f. the plant has characteristic light greenish leaves, whitish flowers with distinct morphology of single main stem with branches coming out of the lower nodes imparting a shape of up-side down open filled umbrella to the canopy allowing equal distribution of sunlight, thus prevents yellowing and fall of lower leaves (FIGS. 1 and 2), g. the plant is able to produce highest herbage, oil and menthol yield per unit area as compared to all other existing varieties.

TABLE 1

Comparative growth and yield characteristics of plant of invention "Sambhav" (GRB 2–18) in relation to the existing Japanese mint varieties

| Property | Himalaya | Shivalik | MAS-1 | Kalka | Gomti | Kosi | Sambhav |
|---|---|---|---|---|---|---|---|
| Plant height (cm) | 60.9 ± 6.2 | 68.25 ± 3.4 | 43.2 ± 1.1 | 51.6 ± 2.7 | 74.2 ± 7.3 | 66.2 ± 3.1 | 73.5 ± 3.3 |
| Canopy (cm) | 62–70 | 50–56 | 40–50 | 40–60 | 70–75 | 65–72 | 85–90 |
| Leaf number | 40.2 ± 4.2 | 49.6 ± 4.8 | 40.0 ± 1.4 | 38 ± 2.0 | 46.0 ± 2.8 | 50.4 ± 3.8 | 44.2 ± 2.2 |
| Branch length | 40.4 ± 6.8 | 44.2 ± 8.7 | 36.6 ± 9.0 | 45 ± 9.7 | 58.4 ± 14.7 | 52.0 ± 5.7 | 50.1 ± 8.8 |
| Branch number | 29.2 ± 4.0 | 22.4 ± 1.7 | 13.6 ± 1.7 | 27.2 ± 1.1 | 28.4 ± 2.9 | 30.4 ± 1.7 | 35.1 ± 2.8 |
| Leaf length | 7.1 ± 0.5 | 7.3 ± 0.3 | 7.5 ± 1.0 | 7.4 ± 0.8 | 7.7 ± 0.6 | 7.40 ± 0.7 | 8.6 ± 0.6 |
| Leaf breadth | 4.5 ± 0.2 | 5.0 ± 0.2 | 3.8 ± 0.5 | 4.0 ± 0.3 | 4.7 ± 0.2 | 4.60 ± 0.5 | 5.50 ± 0.3 |
| Petiole length | 1.75 ± 0.3 | 1.40 ± 0.1 | 1.6 ± 0.5 | 1.5 ± 0.5 | 1.4 ± 0.1 | 1.4 ± 0.3 | 1.70 ± 0.2 |
| Oil % | 0.7 | 0.5 | 0.5 | 0.8 | 0.5 | 0.8 | 0.8 |
| Menthol % | 80 | 77 | 88 | 82 | 73 | 76 | 77 |
| Herbage yield (Q per 100 m$^2$) | 1.25 | 0.75 | 0.50 | 0.80 | 1.60 | 1.70 | 2.10 |
| Oil yield (Kg per 100 m$^2$) | 0.85 | 0.35 | 0.27 | 0.64 | 0.83 | 1.42 | 1.61 |

| Taxonomic description of the mint plant "Sambhav" | |
|---|---|
| 1. Genus | *Mentha* |
| 2. Species | *arvensis* L. |
| 3. Family | Lamiaceae |
| 4. Common name | Japanese mint/corn mint/menthol mint |
| 5. Plant height | 73.5 ± 3.27 cm. |
| 6. Plant canopy | 85–90 cm |
| 7. Growth habit | Erect sturdy main stem, profuse synchronous branching with growth habit giving an up-side-down open filled umbrella shape to the canopy (Drawing sheet #1, Photograph #1 and 2). |
| 8. Stem | Round to quadrangular hard, woody, green (144A), faint purplish red (59B) pigmentation at the base, 5–10 mm thick at 5$^{th}$ internode. |
| 9. Leaf | |
| Colour | Light green (137B) |
| Texture | Moderately thick and rigid |
| Surface | Hairy and rough |
| Shape | Lacerate |
| Margin | Moderately deep serration (14 to 50 number) |
| Tip | Acute |
| Base | Attenuate |
| Size | Moderately broad |
| Petiole length | 1.7 ± 0.17 cm |
| Area | 16.1 cm$^2$ (Average of full branch) |
| Length | 8.56 ± 0.56 cm |
| Width | 5.51 ± 0.34 cm |
| 10. Leaf:stem ratio (w/w) | 1.7 |
| 11. Inflorescence | Indefinite recemose |
| | Total number of florets 20 to 35 |

-continued

Taxonomic description of the mint plant "Sambhav"

12. Flowers

Arranged in whorls surrounding the stem at the base of lateral leaves.
| | |
|---|---|
| Pedicel | Yellow green (145C) |
| Calyx | Four, Yellow green (145B) |
| Corolla | Purplish white (76D), four, fused to a bell shaped corolla tube |
| Anthers | Four, ocidimetary, come out of the corolla tube |
| Stigma | Bifid, Purple (76A) |

13. Oil content in the fresh herb (%) 0.77 to 0.8
14. Oil quality:

| | |
|---|---|
| Menthol content (%) | 75 to 80% |
| Congealing point | 2 to 21° C. |

15. Herbage (Shoot biomass Q/100 m$^2$) 2.10 the prevention of economic loss to the plant. The chromosome number of the plant is 2n=96. The colour codes are in accordance with the "RHS colour chart published by the Royal Horticultural Society, 80 Vincent Square, London SW1P 2PE, 1995.

Evidence of Uniformity and Stability

No variants of any kind (morphological or molecular) has been observed since 1997 indicating the stability and uniformity of the genotype. Further, the comparative herbage and oil yields of "Sambhav" were significantly higher in comparison to other varieties/genotypes in different years and seasons. Due to vigorous vegetative growth this genotype can be harvested earlier without reducing the yield of herbage, oil or menthol. The traits of insect tolerance against S. obliqua is unprecedented and stable.

Statement of Distinction

The genotype "Sambhav" possessing a very high level of insect tolerant character against leaf damage by S. obliqua

TABLE 2

Comparison of "Sambhav" with other existing varieties of the same botanical and market class of Mentha arvensis

| Character | cv.MAS-1 | cv.Kalka | cv.Shivalik | cv.Gomti | cv.Himalaya | cv.Sambhav |
|---|---|---|---|---|---|---|
| 1. Leaf:stem ratio | 1.2 | 1.0 | 0.8 | 1.0 | 1.5 | 1.7 |
| 2. Stem | | | | | | |
| colour | Upper green (141C), lower pigmented red purple (71B) | GREEN (141C), lower pigmented red purple (71B) | Green (141B) lower pigmented red purple (71B) | Green (143B) lower pigmented purple (77A) | Green (143C) lower purplish (70A) | Green (144A) lower purplish (59B) |
| Stiffness | Hard | Hard | Woody | Woody | Hard | Woody |
| Thickness at 5$^{th}$ internode (mm) | 6.8 | 3.6 | 10.0 | 7.9 | 8.0 | 10.0 |
| 3. Leaf | | | | | | |
| Colour | Green (139C) | Green (139C) | Green (138A) | Green (138A) | Green (138B) | Green (137B) |
| Length (cm) | 6.46 | 6.7 | 5.2 | 6.4 | 6.2 | 8.6 |
| Width (cm) | 2.3 | 2.4 | 2.8 | 3.1 | 3.6 | 5.1 |
| Area (cm$^2$) | 8.2 | 8.7 | 10.1 | 13.3 | 15.4 | 16.1 |
| 4. Petiole length (cm) | 1.1 | 1.2 | 0.6 | 0.7 | 1.5 | 1.7 |
| 5. Flower colour | Whitish | Whitish | Whitish | Whitish | Pinkish white | Purplish white (76C) |
| 6. Flower length (mm) | 3.72 | 3.48 | 4.66 | 4.74 | 3.72 | 4.65 |
| 7. Calyx colour | Green (143B) with red purple streaks (71B) | Green (143B) with red purple streaks (71B) | Green (141B) | Green (141B) | Green (143C) | Green (145B) |
| 8. Stigma colour | White | White | Purplish (71C) | Purplish (71C) | White | Purple (76A) |
| 9. Disease incidence to | | | | | | |
| Rust | Tolerant | Resistant | Susceptible | Susceptible | Resistant | Resistant |
| Alternaria leaf blight | | Resistant | Susceptible | Susceptible | Resistant | Resistant |
| Corynespora leaf spot | Susceptible | Tolerant | Susceptible | Susceptible | Tolerant | Tolerant |
| Powdery mildew | Susceptible | Susceptible | Tolerant | Tolerant | Tolerant | Tolerant |
| 10. Pest infestation | | | | | | |
| Spilarctia obliqua | Susceptible | Susceptible | Susceptible | Highly Susceptible | Susceptible | Tolerant |

The plant genotype "Sambhav" developed in the present invention is a herbaceous perennial with a single tall upright stem possessing several lateral branches coming out from the lower nodes laterally rising in a fashion to give a shape of an open filled umbrella turned upside down. This special arrangement of branches facilitates the distribution of the captured sunlight equally to all the leaves and hence avoiding shading thereby, reducing lower leaf fall amounting to larvae is unique and unprecedented not possessed by any known variety. Additionally, it has a distinct canopy of one straight main stem with many lower branches arranged like an open filled umbrella turned upside down which is characteristic to this genotype only. The genotype is having highest biomass and highest oil yield unit area in comparison to others. The total menthol yield of the new genotype is higher per unit area in comparison to other genotypes. Its genetic make up is distinct in terms of DNA profile.

Randomly Amplified Polymorphic DNA analysis: The RAPD profiles of the plant "Sambhav" were unambiguously able to establish its distinct identity as completely different from the parent plant "Himalaya" as well as the known released varieties. The plant of the present invention was developed by screening molecular variants among somaclones already differentiated as distinct, unique and novel at DNA level. The plant is having desirable morphological and economical traits in a rare unmatchable combination and is available only with us in CIMAP. No variation in the RAPD patterns was observed in the analysis of the micropropagated as well as field raised population in successive generations indicating the stability of the genotype. The 20 MAP primers (MAP 01 to MAP 20) with the sequence AAATCGGAGC (SEQ ID NO: 1), GTCCTACTCG (SEQ ID NO: 2), GTCCTTAGCG (SEQ ID NO 3), TGCGCGATCG (SEQ ID NO: 4), AACGTACGCG (SEQ ID NO: 5), GCACGCCGGA (SEQ ID NO: 6), CACCCTGCGC (SEQ ID NO 7), CTATCGCCGC (SEQ ID NO: 8), CGGGATCCGC (SEQ ID NO: 9), GCGAATTCCG (SEQ ID NO: 10), CCCTGCAGGC (SEQ ID NO: 11), CCAAGCTTGC (SEQ ID NO: 12), GTGCAATGAG (SEQ ID NO: 13), AGGATACGTG (SEQ ID NO: 14), AAGATAGCGG (SEQ ID NO: 15), GGATCTGAAC (SEQ ID NO: 16), TTGTCTCAGG (SEQ ID NO: 17), CATCCCGAAC (SEQ ID NO: 18), GGACTCCACG (SEQ ID NO: 19), AGCCTGACGC (SEQ ID NO: 20) and 20 OPJ (Operon Technologies Inc, USA) were used for the analysis and similarity indices were computed to generate similarity matrix among existing varieties and the plant Sambhav (Table 3). The OPJ primers (01 to 20) were procured from Operon technologies, USA. The MAP primers were used to develop a unique and distinct RAPD profile FIG. 7 of the Plant.

TABLE 3

Similarity indices of different control plants analysed in comparison to Sambhav

| Gomti | Himalaya | Kosi | MAS-1 | Kalka | Shivalik | Sambhav |
|---|---|---|---|---|---|---|
| 1.00 | | | | | | |
| 0.90 | 1.00 | | | | | |
| 0.89 | 0.94 | 1.00 | | | | |
| 0.91 | 0.92 | 0.92 | 1.00 | | | |
| 0.85 | 0.88 | 0.85 | 0.89 | 1.00 | | |
| 0.92 | 0.93 | 0.91 | 0.90 | 0.87 | 1.00 | |
| 0.87 | 0.73 | 0.78 | 0.82 | 0.83 | 0.84 | 1.00 |

Figure 1:
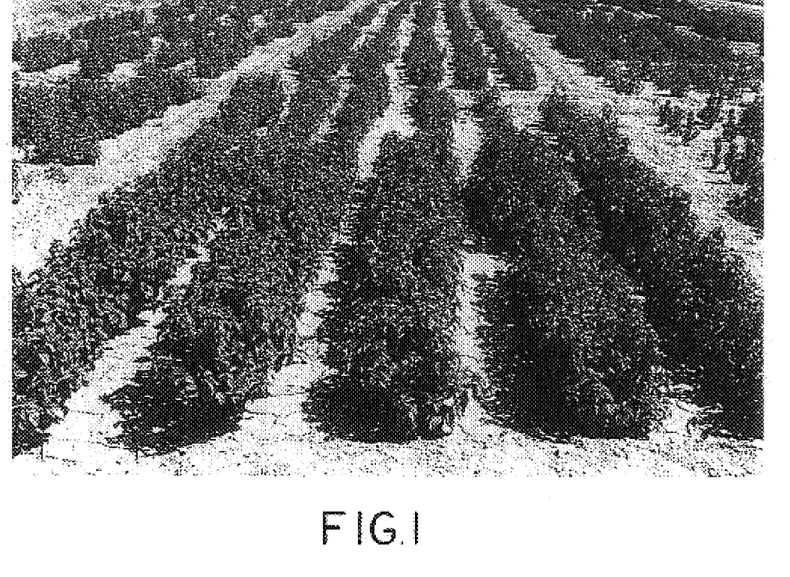
FIG. 1 shows field view of the morphological features of the 'Sambhav' plants at 70 days.

From RAPD analysis the profiles were studied and similarity indices were calculated which were put into a matrix. This matrix was used to produce a graphic phenogram by means of UPGMA (unweighted pair group method with arithmetic average) cluster analysis (FIG. 1). As represented in the phenogram the clone of the invention is quite different from the other varieties. The diversity of the genotype of the plant of invention 'Sambhav' is 13%, 28%, 22%, 18%, 17% and 16% from the varieties Gomti, Himalaya, Kosi, MAS-1, Kalka and Shivalik. Highest 28% difference in terms of polymorphic profiles was observed for the genotype of the invention with the parent plant Himalaya from which it was developed as a somaclone. The plant genotype of the invention 'Sambhav' was most similar in terms of polymorphism with Gomti. In total the distinctiveness of the clone in RAPD profiles was established as total polymorphism detected.

So the protocol for developing insect tolerant plants in vitro can be explained in details as an example of the development of 'Sambhav' which involves following steps and sub-steps.

Example of Development of Insect Tolerant Plant 'Sambhav'.

Step A: Explant, Culture Conditions and Regeneration for Generating Genetically Modified somaclones.

1. The *Mentha arvensis* cv Himalaya explant material was collected from the field grown plants and washed sequentially with 2% detergent, distilled water containing a few drops of Savlon (Johnson and Johnson, India), 0.1% acidified mercuric chloride and autoclaved distilled water. About 1 cm long internode pieces were inoculated in the MS media (Murashige T, Skoog F. 1962. A revised medium for rapid growth and bioassay with tobacco tissue cultures. *Physiol. Planta.* 15:473–497.) containing the auxin, 0.2 µg ml$^{-1}$ 2,4 dichlorophenoxy acetic acid (2,4-D) and the cytokinin, 7 µg ml$^{-1}$ 6-(γγ'-dimethylallyl amino) purine (2iP or 2aP).

2. The cultures were grown at 25±2° C. and 400 to 600 lux light intensity with 16 h photoperiod.

3. The regenerated shoots were separated at 12 weeks from the explant inoculation and transferred to the MS medium free of hormones for rooting.

4. The plantlets thus generated were examined for any genotypic change by comparing their RAPD profiles with that of cv Himalaya using the 12 random decanucleotide primers having the sequences AAATCGGAGC (SEQ ID NO: 1), GTCCTACTCG (SEQ ID NO: 2), GTCCTTAGCG (SEQ ID NO: 3), TGCGCGATCG (SEQ ID NO: 4), AACGTACGCG (SEQ ID NO: 5), GCACGCCGGA (SEQ ID NO: 6), CACCCTGCGC (SEQ ID NO: 7), CTATCGCCGC (SEQ ID NO: 8), CGGGATCCGC (SEQ ID NO: 9), GCGAATTCCG (SEQ ID NO: 10), CCCTGCAGGC (SEQ ID NO: 11), CCAAGCTTGC (SEQ ID NO: 12).

5. We obtained 245 molecular variants after screening 3000 regenerated clones. Out of 245 clones 155 clones were different from 'Himalaya' with one primer out of the 12 primer used. Eighty-two variants were different from 'Himalaya' with two primers and the rest 8 variants with three or more primers.

Step B: Screening Genetically Modified Somaclones for Spilarctia Obliqua Tolerance 1. The individual molecular variants selected through RAPD analysis of regenerated clones were multiplied from the internode segments, which were inoculated in MS based media containing vitamins, 100 µg ml$^{-1}$ myo-inositol, 3% wv$^{-1}$ sucrose, 1.5% wv$^{-1}$ agar (Difco), 0.5 µg ml$^{-1}$ NAA (1-napthalene acetic acid) and 5 µg ml$^{-1}$ BAP (6-benzyl aminopurine).

2. The cultures were grown at 25±2° C. and 400 to 600 lux light intensity with 16 h photoperiod.

3. These clones from individual variants were tested for uniformity through RAPD profiling after isolating DNA from 40 mg of tissue, using the random primers (AAATCGGAGC (SEQ ID NO; 1), GTCCTACTCG (SEQ ID NO: 2), GTCCTTAGCG (SEQ ID NO: 3), TGCGCGATCG (SEQ ID NO: 4), AACGTACGCG (SEQ ID NO: 5), GCACGCCGGA (SEQ ID NO: 6), CACCCTGCGC (SEQ ID NO: 7), CTATCGCCGC (SEQ ID NO: 8), CGGGATCCGC (SEQ ID NO: 9), GCGAATTCCG (SEQ ID NO: 10), CCCTGCAGGC (SEQ ID NO: 11), CCAAGCTTGC (SEQ ID NO: 12)).

Figure 5:
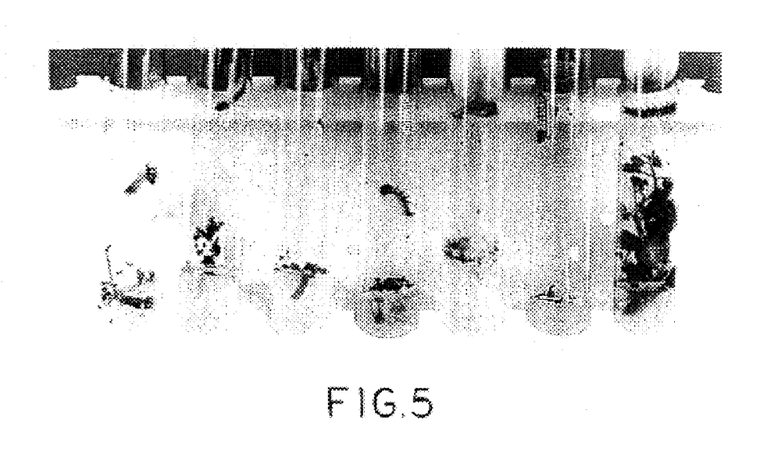
FIG. 5 shows instar larvae infected individual clones of other plants in comparison with clone of 'Sambhav'.
Figure 6:
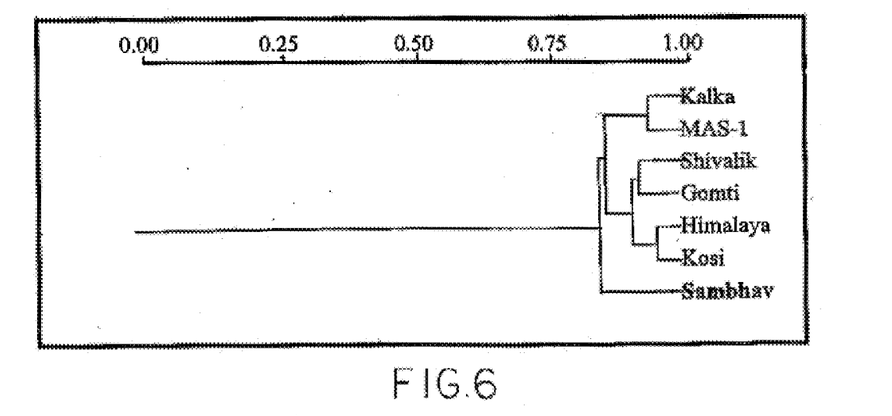
FIG. 6 shows the genetic similarity of the new clone 'Sambhav' with other varieties of Mentha arvensis.

4. These regenerated shoots were grown in MS medium without growth hormones for rooting for 12 weeks.
5. The variants were then subjected to screening against the larvae of lepidopteran insect pest *Spilarctia obliqua* in replicates.
6. The in vitro growing genetically distinct clones were subjected to feeding attack by actively feeding $3^{rd}$ instar larvae by releasing them right in the culture tubes containing individual clones on the rooting medium (FIG. 5). Most of the shoots of the clones were eaten away by these larvae within 2–3 days. However, three clones clones (CIMAP/GRB 1-06, 2-18 and 5-15) showed the least feeding by the larvae. In these tubes, only initial bites could be observed and non-feeding was also conspicuous by typical symptoms of no growth in the starved larvae.
7. These larvae were then transferred to other clone tubes, where they resumed feeding. This led to us to believe that the three clones must have some characteristics not liked by the feeding larvae.
8. We again confirmed this by releasing another set of actively feeding $4^{th}$ instar larvae into the tubes containing these three identified clones.
9. This was repeated three times and each time, the larvae showed non-preference and stopped feeding.
10. These three clones were then hardened and planted in the earthen pots in the glasshouse and observed initially for the growth characters. The growth of the clone GRB 2-18 was more vigorous compared to the other clones and the parent plant Himalaya.
11. These were covered with nets individually and 10 insect larvae per plant were released to assay the leaf damage.
12. Initial insect bite and nonfeeding of insect was observed in the clone GRB 1-06, 2-18 and 5-15 and the magnitude of leaf damage was estimated to be 10%, 5% 20% respectively and 50% for the plant 'Himalaya'.
13. So the clone GRB 2-18 was finally selected for field trials against the check varieties (Gomti, Kalka, Kosi, Himalaya and MAS-1) which showed vigorous growth and better yield of herbage and oil.

Comparison of Sambhav with the Check Varieties

Figure 3:
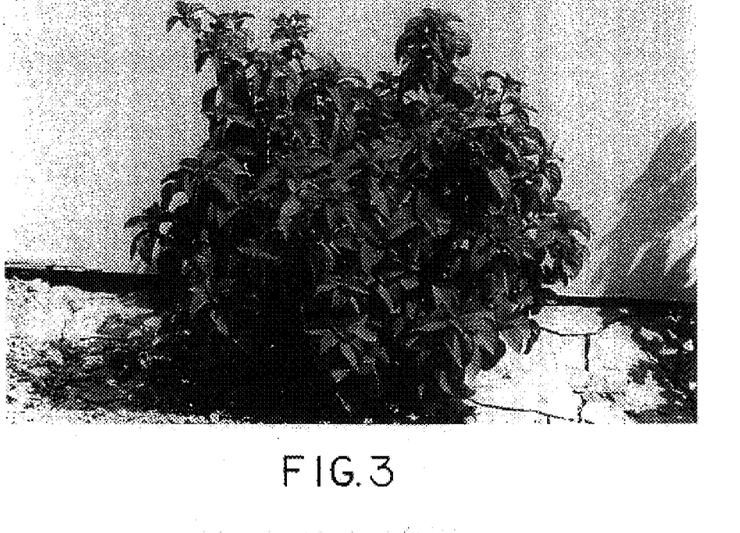
FIG. 3 shows the rapid growth of the 'Sambhav' plant and canopy at 70 days.
Figure 4:
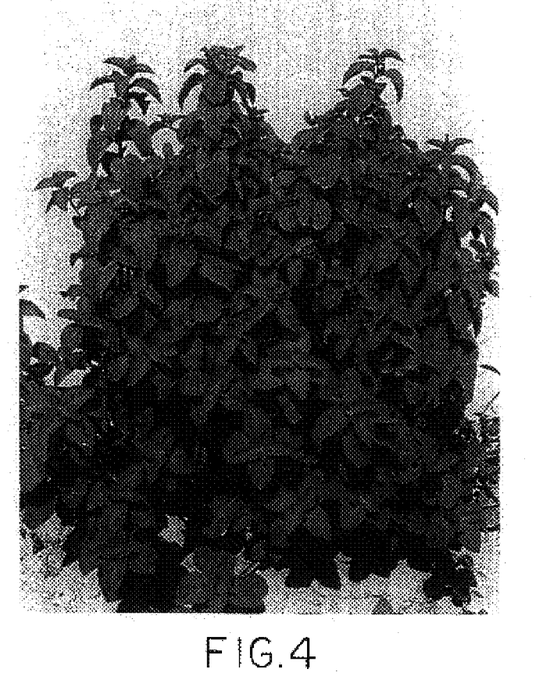
FIG. 4 shows the rapid growth of the 'Sambhav' plant and its canopy at 100 days.

The new genotype GRB 2-18 named as 'Sambhav' was so rapidly growing that it could cover the inter-row spacing of 80 cm completely within a period of 90–100 days, which was not the case of other control varieties taken (FIGS. 3 and 4). The plant canopy covered a space of 85 to 90 cm in 110 days in comparison to Himalaya(62–70 cm), Shivalik (50–56 cm), Gomti (70–75), Kosi (65–72), Kalka (40–60 cm) and MAS-1 (40–50 cm). The herbage yield of the plant 2.8 Q per 100 $m^2$ against 1.25, 0.75, 0.50, 0.80, 1.60, 1.70 for Himalaya, Shivalik, MAS-1, Kalka, Gomti and Kosi. Similarly the oil yield was highest (0.8%) in case of the genotype. The genotype though has less menthol percentage, when the total menthol yield per 100 $m^2$ is estimated by converting the total oil yield per 100 $m^2$ against the menthol percentage (77×1.61/100) and it comes to 1.24 kg, which is much higher than other varieties. The menthol yield values for other varieties are 0.68, 0.27, 0.24, 0.52, 0.60, 1.08 kg per 100 $m^2$ for Himalaya, Shivalik, MAS-1, Kalka, Gomti and Kosi respectively. This was the most desirable economical advantage to the plant with commercial value as it produced highest amount of herbage and ultimately the oil and menthol per unit area in comparison to other genotypes while being the most tolerant to insect pest attack.

The invention claimed is:

1. An in vitro screening method for identifying insect tolerant genotypes or clones, said method comprising the steps of:
   a) growing plantlets in an in vitro system;
   b) screening the plantlets for molecular variation of somaclones using RAPD analysis in vitro;
   c) selecting the somaclones having molecular variation;
   d) exposing the somaclones of step c) to insect larvae or nymphs; and
   e) identifying the surviving somaclones.

2. The method according to claim 1, further comprising growing the surviving somaclones into adult plants.

3. The method according to claim 1 wherein the somaclones are somaclones of *Mentha arvensis*.

4. The method according to claim 1, wherein the insect larvae is *Spilarctia obliqua*.

5. The method according to claim 1, wherein the inset larvae is third or fourth instar larvae.

6. The method according to claim 1, wherein the somaclones are generated vegetatively by tissue culture, glass house, or in the field by asexual reproduction methods.

7. An in vitro screening method for identifying insect tolerant genotypes or clones, said method comprising the steps of:
   a) growing plantlets in an in vitro system;
   b) screening the plantlets for molecular variation of somaclones using RAPD analysis in vitro;
   c) selecting the somaclones having molecular variation;
   d) exposing the somaclones of step c) to insect larvae or nymphs;
   e) identifying the surviving somaclones; and
   f) growing the surviving somaclones into adult plants.

8. An in vitro screening method for identifying insect tolerant genotypes or clones, said method comprising the steps of:
   a) growing plantlets in an in vitro system;
   b) screening the plantlets for molecular variation of somaclones of *Mentha arvensis* using RAPD analysis in vitro;
   c) selecting the somaclones of *Mentha arvensis* having molecular variation;

d) exposing the somaclones of step c) to insect larvae or nymphs;
e) identifying the surviving somaclones of *Mentha arvensis*; and
f) growing the surviving somaclones into adult *Mentha arvensis* plants.

* * * * *